United States Patent
Boland et al.

(10) Patent No.: US 11,165,722 B2
(45) Date of Patent: **\*Nov. 2, 2021**

(54) COGNITIVE MESSAGING WITH DYNAMICALLY CHANGING INPUTS

(71) Applicant: International Business Machines Corporation, Armonk, NY (US)

(72) Inventors: Gregory F. Boland, Katonah, NY (US); Kristina M. Brimijoin, Hastings-on-Hudson, NY (US); Avraham Leff, Spring Valley, NY (US); Yu Ma, White Plains, NY (US); Russell G. Olsen, Flower Mound, TX (US); James T. Rayfield, Ridgefield, CT (US); Katherine Vogt, New York, NY (US); Justin D. Weisz, Stamford, CT (US)

(73) Assignee: International Business Machines Corporation, Armonk, NY (US)

( * ) Notice: Subject to any disclaimer, the term of this patent is extended or adjusted under 35 U.S.C. 154(b) by 276 days.

This patent is subject to a terminal disclaimer.

(21) Appl. No.: 15/197,067

(22) Filed: Jun. 29, 2016

(65) Prior Publication Data

US 2018/0004725 A1  Jan. 4, 2018

(51) Int. Cl.
*G06F 17/27* (2006.01)
*G06F 19/00* (2018.01)
(Continued)

(52) U.S. Cl.
CPC ............ *H04L 51/02* (2013.01); *G06F 17/277* (2013.01); *G06F 17/279* (2013.01); *G06F 19/00* (2013.01); *G06F 19/3418* (2013.01); *G06Q 10/103* (2013.01); *G06Q 10/107* (2013.01); *G06Q 10/1093* (2013.01); *G16H 10/60* (2018.01); *H04L 67/306* (2013.01); *G16H 10/20* (2018.01); *G16H 40/20* (2018.01); *H04L 51/16* (2013.01)

(58) Field of Classification Search
CPC .......... H04W 4/12; G06N 3/006; H04I 51/02; G06F 40/35
USPC ................................ 715/763–765, 740, 851
See application file for complete search history.

(56) References Cited

U.S. PATENT DOCUMENTS 6,699,195 B2   3/2004 Nanazawa et al.
7,315,825 B2   1/2008 Rosenfeld et al.
(Continued)

OTHER PUBLICATIONS

IBM, "Application of a Single Moveable Input Box to Allow Concise Realtime Instant Multi-Threaded Messaging", http://IP.com/IPCOM/000193027D, Feb. 8, 2010, pp. 1-8.
(Continued)

*Primary Examiner* — Cao H Nguyen
(74) *Attorney, Agent, or Firm* — Steven M. Bouknight

(57) ABSTRACT

An embodiment of the invention provides a method for sending a message from a first user to a second user where an interface receives a message from the second user. A processor connected to the interface identifying one or more keywords in the message and searches an electronic database for the keyword(s) to identify one or more scripted message for the keyword(s). The electronic database includes scripted messages for each keyword in the electronic database. A communications device connected to the processor sends the identified scripted message(s) to the second user.

20 Claims, 7 Drawing Sheets

(51) Int. Cl.
| | |
|---|---|
| *G06Q 10/10* | (2012.01) |
| *G16H 10/60* | (2018.01) |
| *H04L 12/58* | (2006.01) |
| *H04L 29/08* | (2006.01) |
| *G16H 10/20* | (2018.01) |
| *G16H 40/20* | (2018.01) |

(56) References Cited

U.S. PATENT DOCUMENTS

| | | | |
|---|---|---|---|
| 7,743,340 B2 | 6/2010 | Horvitz et al. | |
| 7,967,749 B2 | 6/2011 | Hutchinson et al. | |
| 7,996,240 B2 | 8/2011 | Canda | |
| 8,374,988 B2 | 2/2013 | Gawlick | |
| 8,417,662 B2 | 4/2013 | Gawlick | |
| 8,428,632 B2 | 4/2013 | Ye et al. | |
| 8,489,428 B2 | 6/2013 | Brown | |
| 8,554,195 B2 | 10/2013 | Rao | |
| 8,847,767 B2 | 9/2014 | Lim et al. | |
| 8,880,454 B2 | 11/2014 | Christie, IV et al. | |
| 8,930,223 B2 | 1/2015 | Friedlander et al. | |
| 8,940,908 B2 | 2/2015 | Faroog et al. | |
| 8,996,428 B2 | 3/2015 | Baras et al. | |
| 2,015,054 A1 | 4/2015 | Lara et al. | |
| 9,015,054 B2 | 4/2015 | Lara | |
| 9,113,776 B2 | 8/2015 | Connor | |
| 9,250,104 B2 | 2/2016 | Greiner et al. | |
| 9,298,882 B2 | 3/2016 | Proud | |
| 10,176,300 B1 | 1/2019 | South | |
| 10,529,446 B2 | 1/2020 | Boland | |
| 2004/0171918 A1 | 9/2004 | Suzuki et al. | |
| 2008/0045236 A1* | 2/2008 | Nahon | H04W 4/12 455/456.1 |
| 2009/0043608 A1* | 2/2009 | Nadas | G06Q 10/0631 705/3 |
| 2011/0202490 A1 | 8/2011 | Gawlick | |
| 2012/0004924 A1 | 1/2012 | Kachnowshi et al. | |
| 2012/0209650 A1 | 8/2012 | Romagnino | |
| 2013/0179176 A1 | 6/2013 | Gotthardt | |
| 2013/0197369 A1 | 8/2013 | Xiang | |
| 2013/0223606 A1 | 8/2013 | Lee | |
| 2013/0246512 A1* | 9/2013 | Lawler | G06N 3/006 709/203 |
| 2013/0266795 A1 | 10/2013 | Consentino et al. | |
| 2013/0311193 A1 | 11/2013 | Know et al. | |
| 2014/0025393 A1 | 1/2014 | Wang et al. | |
| 2014/0113263 A1 | 4/2014 | Jarrell | |
| 2014/0114142 A1 | 4/2014 | Shaoulian | |
| 2014/0129249 A1 | 5/2014 | Nkoy et al. | |
| 2014/0278544 A1 | 9/2014 | Khurana et al. | |
| 2014/0297301 A1 | 10/2014 | Rock | |
| 2014/0344718 A1* | 11/2014 | Rapaport | H04L 51/32 715/753 |
| 2014/0348318 A1 | 11/2014 | Talapady et al. | |
| 2015/0000904 A1 | 1/2015 | Proud | |
| 2015/0125832 A1 | 5/2015 | Tran | |
| 2015/0127385 A1 | 5/2015 | Pecora | |
| 2015/0194071 A1 | 7/2015 | Bennett | |
| 2015/0297904 A1 | 10/2015 | Kavounas | |
| 2015/0359966 A1 | 12/2015 | Day et al. | |
| 2016/0308794 A1* | 10/2016 | Kim | H04L 51/046 |
| 2017/0262604 A1 | 9/2017 | Francois | |
| 2018/0006972 A1 | 1/2018 | Boland | |
| 2018/0181711 A1 | 6/2018 | Boland | |
| 2018/0181721 A1 | 6/2018 | Boland | |
| 2018/0181722 A1 | 6/2018 | Boland | |
| 2020/0111550 A1 | 4/2020 | Boland | |

OTHER PUBLICATIONS

Anonymously, "System, Method and Appratus for Providing Per-Contact Status Information within an Instant-Messaging System", http://IP.com/IPCOM/000215762, Mar. 11, 2012, pp. 1-5.

Office Action in U.S. Appl. No. 15/198,381; dated May 1, 2018; pp. 1-11.

Office Action in U.S. Appl. No. 15/198,381; dated Sep. 10, 2018; pp. 1-9.

List of IBM Patents or Applications Treated as Related.

List of IBM Patents or Patent Applications Treated as Related, Sep. 13, 2017, 2 pages.

Mell, Peter et al., "The NIST Definition of Cloud Computing", National Institute of Standards and Technology, Information Technology Laboratory, Version 15, Oct. 7, 2009, 2 pages.

Wolman, Alec et al., "Using Trusted Sensors to Monitor Patients' Habits", Research.microsoft.com; healthsec-2010, Jan. 2010, 2 pages.

Office Action in U.S. Appl. No. 15/387,760; dated Mar. 11, 2019; pp. 1-19.

IBM et al., "Application of a Single Moveable Input Box to Allow Concise Realtime Instant Multi-threaded Messaging", IP.com Prior Art Database Technical Disclosure, Feb. 8, 2010, 8 pages, IBM.

Kramer Technologies, "Patient Registration Systems," http://www.kramergroup.com/patient-registration-system.html, Aug. 30, 2016, 1 page, Kramer Technologies, Orlando, FL.

IBM et al., "System, Method and Apparatus for Providing Per-contact Status Information Within an Instant-Messaging System", IP.com Prior Art Database Technical Disclosure, Mar. 11, 2012, 5 pages, IBM.

Spela Kosir, "Wearables in Healthcare", https://www.wearable-technoligies.com/2015/04/wearables-in-healthcare/, 3 pages, Apr. 15, 2015, Wearable Technologies.

IBM: List of IBM Patents or Patent Applications Treated as Related (Appendix P), Sep. 10, 2020, 2 pages.

USPTO, Final Rejection Office Action, dated Aug. 24, 2020, 32 Pages, U.S. Appl. No. 15/387,955.

* cited by examiner

COGNITIVE MESSAGING WITH DYNAMICALLY CHANGING INPUTS

BACKGROUND

The present invention relates to systems, methods, and computer program products for cognitive messaging with dynamically changing inputs. Instant messaging and electronic mail, most commonly referred to as e-mail or email, is a way of exchanging digital messages from an author to one or more recipients. Email operates across computer networks ranging from local area networks (LAN) to broad-ranging networks, such as the Internet. Email provides a quick and efficient means for people to electronically communicate, whether they are located in the same building or thousands of miles apart.

SUMMARY OF THE INVENTION

An embodiment of the invention provides a method for sending a message from a first user to a second user where an interface receives a message from the second user. A processor connected to the interface identifying one or more keywords in the message and searches an electronic database for the keyword(s) to identify one or more scripted message for the keyword(s). The electronic database includes scripted messages for each keyword in the electronic database. A communications device connected to the processor sends the identified scripted message(s) to the second user.

Another embodiment of the invention provides a method for communicating with a user where a change to a profile of a user is identified. An electronic database is searched for the change to identify one or more scripted messages for the change. The electronic database includes scripted messages for each change. The identified scripted message(s) are automatically sent to the user.

BRIEF DESCRIPTION OF THE SEVERAL VIEWS OF THE DRAWINGS

The present invention is described with reference to the accompanying drawings. In the drawings, like reference numbers indicate identical or functionally similar elements.

DETAILED DESCRIPTION

Figure 1:
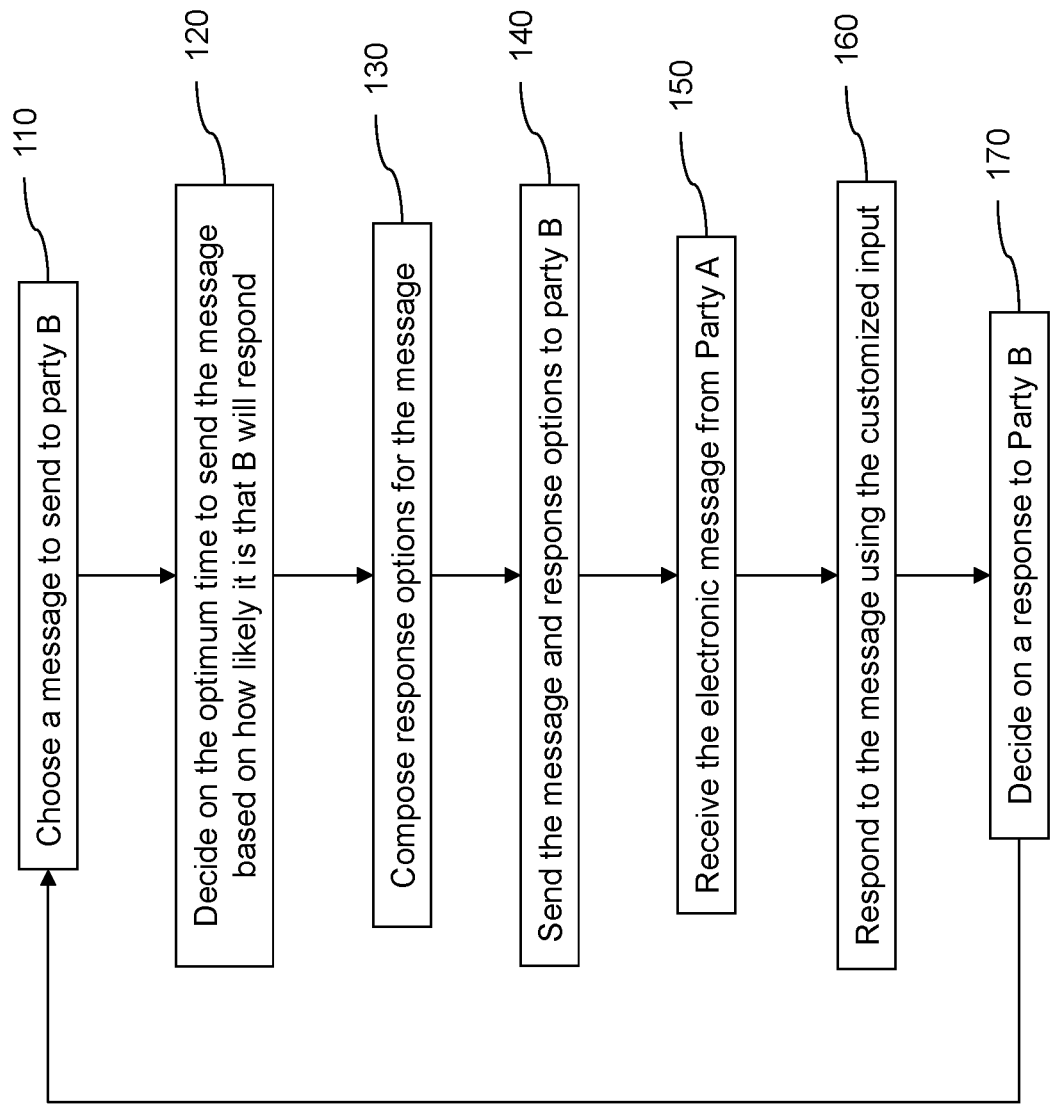
FIG. 1 is a flow diagram illustrating a method for cognitive messaging with dynamically changing inputs according to an embodiment of the invention.

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

At least one embodiment of the invention provides a digital communication system that uses cognitive agents to enhance the communication by deciding what messages to send, when to send messages, and specifying response options for a particular message. In the system, a single chat "entity" may consist of one human working with one cognitive agent (CA). For example, in a two party chat, Party A may consist of Human_A and CA_A, and Party B may consist of Human_B and CA_B. On both sides of the communication, either a human or cognitive agent can send messages in the chat.

Human users may send self-composed messages in the chat system. In addition, the system can supports scripted messages, which can include a hierarchical tree of messages (e.g., a conversation tree or dialogue tree). Each message in the tree can be affected by how the user responds to the previous message. For example, if a user answers choice "B" to the first message, then the traversal of the tree could be interrupted and moved to a different section of messages, continue to the second message, insert a new script, or even trigger an end to the script. Each message in the tree to has at least one of these actions.

For each message (e.g. "How sad are you feeling today?"), the scripted messages can include a fixed set of response options (e.g., "Not sad at all", "A little sad", "Very sad"). Response options may consist of freeform text, single select, multi-select, numerical input, numerical range, date input, images, audio, videos, etc.

Scripted messages may be sent by humans (manually) or by CA's based on the result of an analytic process. Based on the content of prior messages in the chat, natural language processing techniques can be used to parse the content of previous chat messages and generate a response. For example, if a person says "I am feeling sad today", a cognitive agent may compare the content of that message to scripted messages in a database, triggering a script that checks for depression, asking questions like "Did you feel sad yesterday?" and "How sad do you feel today?"

In at least one embodiment, scripted messages are based on information in an external data source, where analytics running on external data that is associated with a party in the chat triggers the generation of a message in chat. For example, a wellness application is tracking the weight of a cardiac patient on a daily basis. When the patient's weight significantly increases (e.g., more than 3 lbs in 1 day), the cognitive agent may trigger a scripted message in the chat asking the patient "how are you feeling today?"; "Have you changed anything in your diet?"; and/or, "When was the last time you used the restroom?"

Another example is a hospital analytics system that wants to know if a congestive heart failure (CHF) patient has experienced certain symptoms. The Hospital party (either human or CA) may initiate a question asking, "What symptoms have you experienced today?" with multi-select response options of "swelling", "tiredness", and "confusion". After the patient responds "swelling" and "tiredness", a follow-up question in the conversation script may ask the patient to explain their activities that day in free form text. The user interface for input can update to a text field in relation to the corresponding message.

Another example shows how local data sources may be used by a cognitive agent to generate response options for a given question. A medical system needs to schedule a patient for a doctor's appointment and can send a message to the patient asking "When are you free to meet with the doctor tomorrow?" A cognitive agent acting on behalf of the patient may parse this question, determine that it is about scheduling, and consult the patient's calendar (e.g., when embodied on a mobile device, the chat application may be given calendar read access). The cognitive agent may find one or more free times and generate response options for the patient to manually review. In another embodiment, the patient may specify a preference for the cognitive agent to automatically send a response without prior review.

FIG. 1 is a flow diagram illustrating a method for cognitive messaging with dynamically changing inputs according to at least one embodiment of the invention. Although this example illustrates communication between two parties, the system can facilitate communication between more than two parties. Party A (cognitive agent or human) can choose a message to send to party B 110. Party A can decides on the optimum time to send the message based on how likely it is that B will respond, based on the history of B's responses (e.g., the times at which B responded) 120. Party A can compose the response options (i.e., multiple selection, yes/no, free form text) for the message 130. Party A can send the message and response options to party B 140.

Party B (human or cognitive agent) can receive the electronic message from Party A 150. The input section of Party B's user interface can dynamically change to provide the response options which Party A has specified. Party B can respond to the message using the customized input 160. Party A's cognitive agent can then decide on a response to Party B and returns to step 110, if necessary 170.

At least one embodiment of the invention includes a chat user interface that enables one party to send scripted messages with pre-defined response formats, and a dynamically-adjusting user interface based on the type of the response required (e.g., multi-select, single-select, free response, numerical input, date input, image, video, audio, etc.). The system can include cognitive agents on both Party A side (initiator) and Party B side (responder) that use analytics on chat content and/or external data sources (e.g., health care records, calendars) to generate messages and/or responses to messages.

The system can learn the optimum time to message a person based on the person's response history. A dialogue script can be defined as a graph whose nodes are sent messages and whose edges are responses to those messages. The nodes and edges can be pre-defined where the nodes can be associated with meta-information for rendering in the user interface. This can allow dynamic (unscripted) communication to be mapped to a given node and/or edge.

Figure 2:
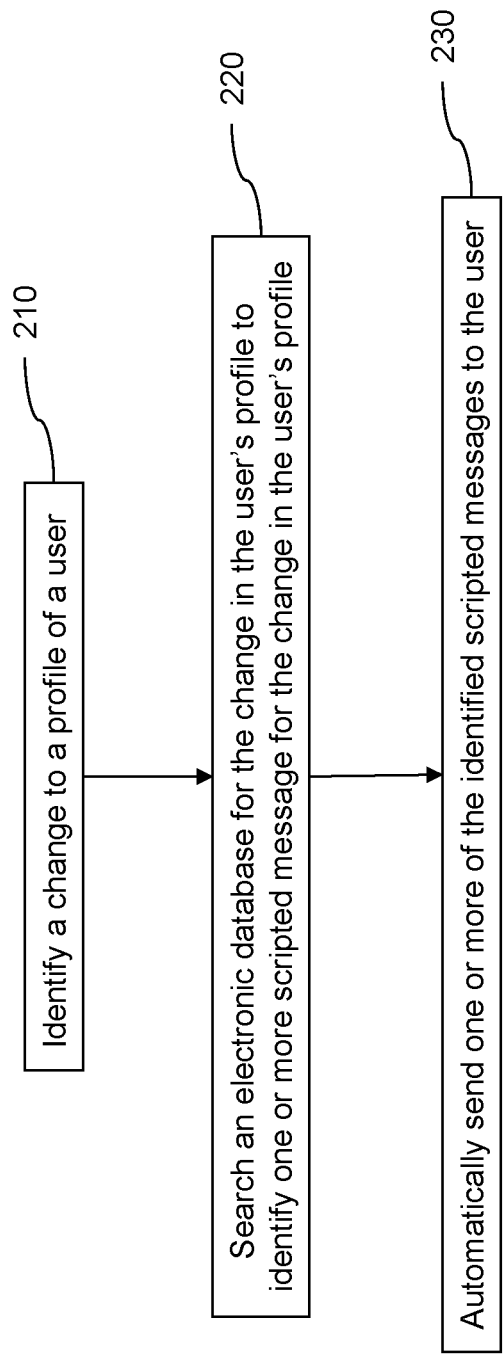
FIG. 2 is a flow diagram illustrating a method for communication with a user according to another embodiment of the invention.

FIG. 2 is a flow diagram illustrating a method for cognitive messaging with dynamically changing inputs according to an embodiment of the invention. A processor can identify a change to a profile of a user 210, such as an addition to the user's profile and/or a deletion to the user's profile. For example, the processor can identify that the user's medical record has been updated to list that he is experiencing symptoms of depression.

The processor can search an electronic database for the change in the user's profile to identify one or more scripted message for the change in the user's profile 220. The electronic database can include scripted messages for each change. For example, the scripted messages include "How are you feeling today?", "Have you taken your medication today?", and "Would you like to schedule an appointment to see your doctor?" A communications device connected to the processor can automatically send one or more of the identified scripted messages to the user 230.

In at least one embodiment, the electronic database can also include scripted replies to the scripted messages. For example, the scripted replies include "I am feeling good", "I am feeling ok", "I am not feeling good", "I have taken my medication", and "I need to refill my prescription". The processor can automatically send the scripted replies to the user with the scripted messages.

Figure 3:
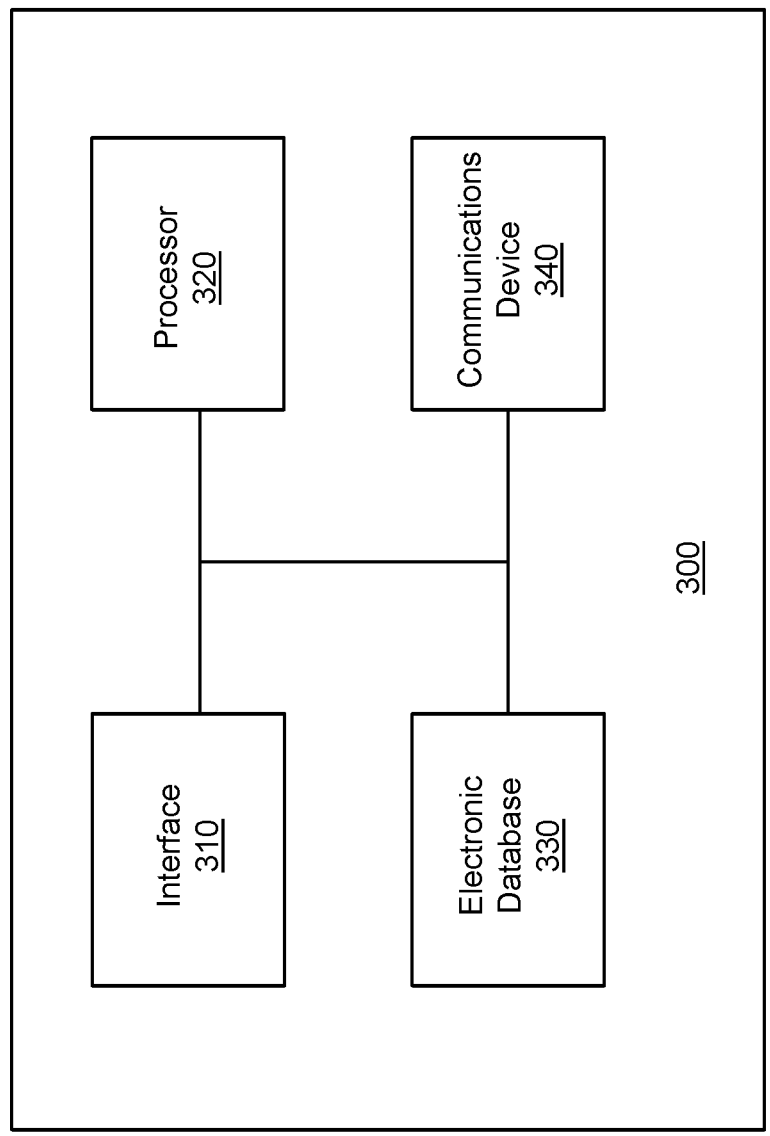
FIG. 3 is a diagram illustrating a system for communication between a first and a second user according to an embodiment of the invention.
Figure 4:
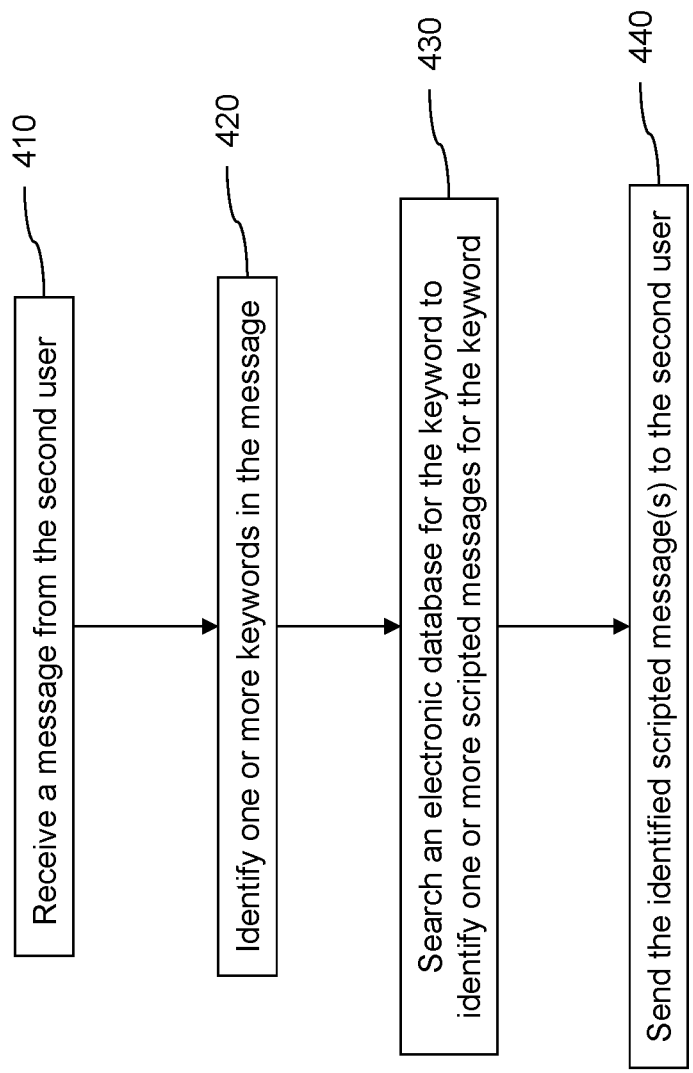
FIG. 4 is a flow diagram illustrating a method for communication between a first and a second user according to an embodiment of the invention.

FIG. 3 is a diagram illustrating a system 300 for communication between a first and a second user according to at least one embodiment of the invention. FIG. 4 is a flow diagram illustrating a method for communication between a first and a second user according to at least one embodiment of the invention, for example, using the system 300. An interface 310 receives a message from the second user (410). As used herein, the term "interface" includes a computer hardware device, such as, for example, a keyboard, a mouse, a microphone, a touchpad, a touchscreen, a joystick, a controller, a camera, a disk drive, an input port, antenna, etc.

A processor 320 connected to the interface 310 can identify one or more keywords in the message (420). For example, the interface 310 receives the message "What symptoms have you experienced today?" and, the processor 320 identifies the keyword "symptoms". As used herein, the term "processor" includes a computer hardware device, such as, for example, a central processing unit (CPU), an integrated circuit, or a microprocessor. As used herein, the term "connected" includes operationally connected, logically connected, in communication with, physically or wirelessly connected, engaged, coupled, contacts, linked, affixed, and attached.

The processor 320 can search an electronic database 330 connected to the processor 320 for the keyword to identify one or more scripted messages for the keyword (430), where the electronic database 330 can include scripted messages for each keyword. For example, for the keyword "symptoms", the electronic database 330 includes the scripted messages "swelling", "tiredness", and "confusion".

A communications device 340 connected to the electronic database 330 can send the identified scripted message(s) to the second user (440). In at least one embodiment, the processor 320 displays the identified scripted messages to the first user (e.g., "swelling", "tiredness", and "confusion"); and, the interface 310 receives one or more selected scripted messages from the first user (e.g., "swelling" and "tiredness"). The communications device 340 can send the selected scripted messages to the second user. In another embodiment, the communications device 340 automatically sends the identified scripted message(s) without instruction from the first user. For example, when the electronic database 330 only includes one scripted message for a keyword, then the communications device 340 can automatically send the selected scripted message to the second user without input from the first user.

In at least one embodiment of the invention, the processor 320 searches a calendar of the first user when the keyword indicates a scheduling question and identify one or more available time slots in the user's calendar. The calendar can be stored on a server and/or on a personal device of the user. A message identifying the available time slot(s) can be automatically sent to the second user and/or the available time slot(s) can be displayed to the first user. For example, identification of the keywords "schedule" and/or "appointment" in the message from the second user triggers a search of the first user's calendar, which determines that the first user has available time slots at 10:00 AM on Thursday and 2:00 PM on Saturday. These time slots can be displayed to the first user and/or automatically sent to the second user without input from the first user.

In at least one embodiment, the processor 320 searches a user's medical records when the keyword indicates a medical question, and identifies one or more entries in the user's medical records that is responsive to the medical question. For example, identification of the keyword "allergic" in the message from the second user triggers a search of the first user's medical records, which determines that the first user is allergic to "pollen" and "Penicillin". A message including the entry in the first user's medical records can be automatically sent to the second user without input from the first user.

In at least one embodiment, the electronic database 330 includes scripted messages, as well as scripted replies to the scripted messages. For example, the electronic database 330 includes the scripted message "swelling" for the keyword "symptoms", and the scripted replies "apply cold therapy", "take medication", and "how long have you been experiencing swelling?" for the scripted message "swelling". The scripted replies can be automatically sent to the second user when the scripted message is sent to the second user.

In at least one embodiment, the processor 320 determines an optimum time to send a message to a recipient (e.g., the first user or the second user) based on a response history of the recipient. The system can create and maintain a log (e.g., in the electronic database 330) that records the time of day that a recipient responds to each message. Based on the log, the processor 320 can identify the time of day that the recipient responds to messages the most often and determine that the optimum time to send a message to a recipient is immediately before this identified time of day (e.g., 5-10 minutes prior to the identified time of day). As used herein, the optimum time to send the message refers to the best time to send the message in order to get a quick response from the recipient.

At least one embodiment of the invention provides a method for communicating with a user where a change to a profile of a user is identified with a monitoring device (e.g., processor). The change to the user's profile can include an addition to the profile and/or a deletion to the profile.

A processor can search an electronic database connected to the processor for the change to identify one or more scripted message for the change. The electronic database can include scripted messages for each change of profile for a user and scripted replies to the scripted messages. A communications device connected to the processor and/or electronic database can automatically send the identified scripted message(s) and/or a plurality of scripted replies from the electronic database to the scripted message to the user.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 5:
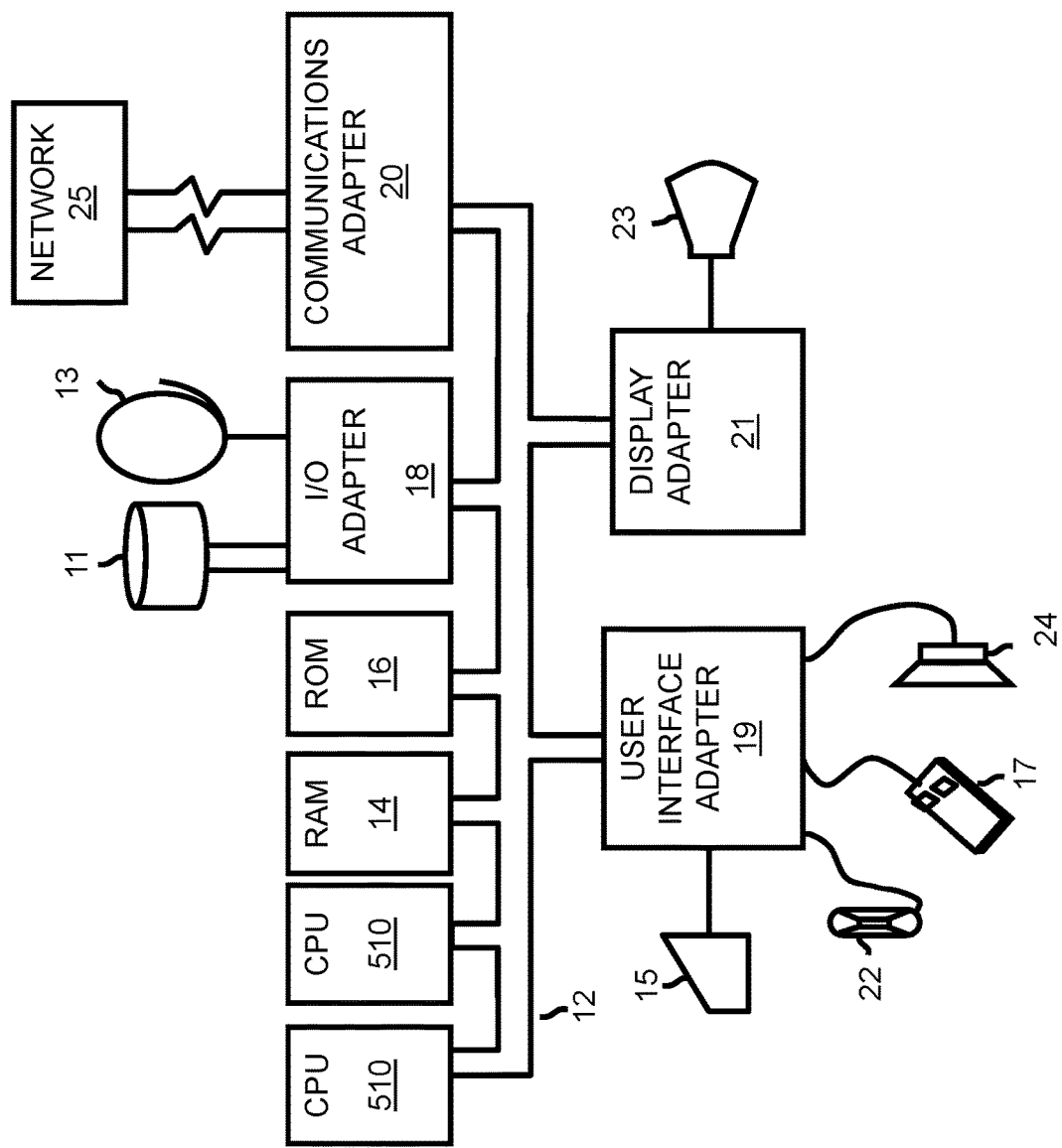
FIG. 5 is a diagram illustrating a computer program product for cognitive messaging with dynamically changing inputs according to an embodiment of the invention.

Referring now to FIG. 5, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 510. The CPUs 510 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
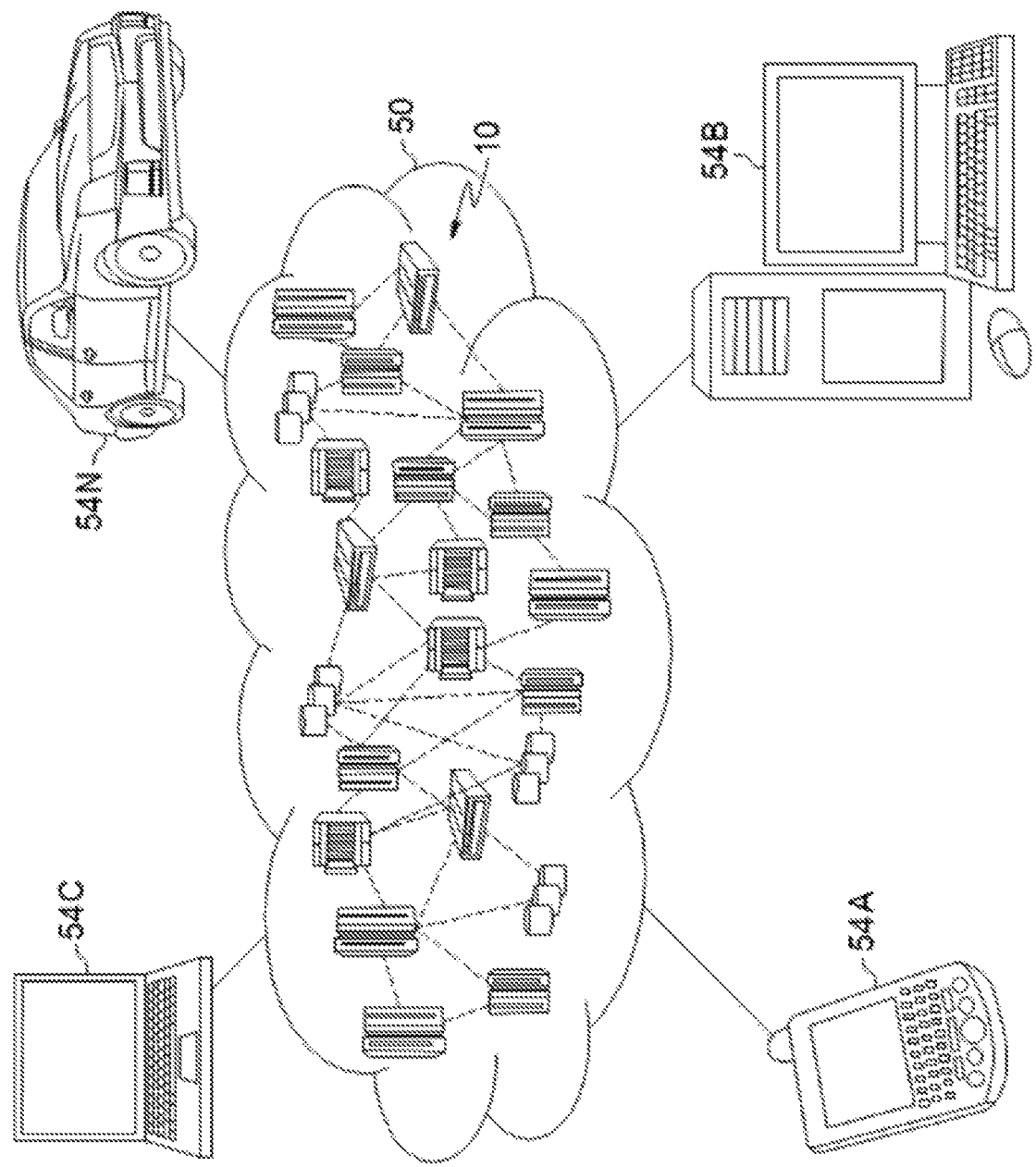
FIG. 6 depicts a cloud computing environment according to an embodiment of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
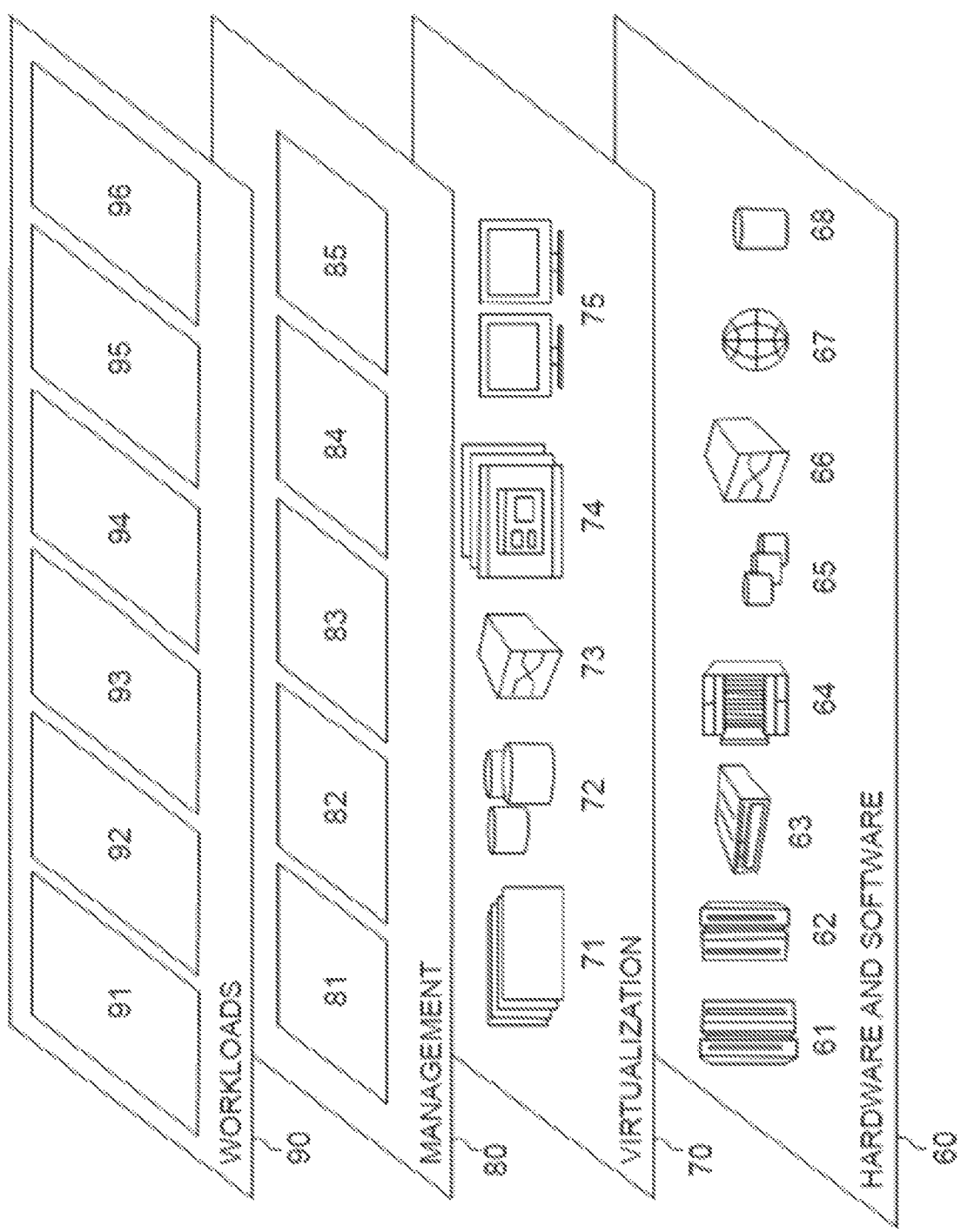
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and cognitive messaging with dynamic inputs 96.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for sending a message from a first user to a second user, said method comprising:
receiving by a first user at an interface of a first user device a message sent from the second user to the first user;
identifying at least one keyword in the message by a processor;
searching an electronic database for the at least one keyword to identify a reply message to the received message, wherein searching the electronic database comprises searching a user's medical records when the at least one keyword indicates a medical question, wherein the reply message comprises at least one scripted message having contents corresponding to a response to information contained in the received message, the electronic database including scripted messages for each keyword in the electronic database, and wherein identifying the reply message comprises identifying at least one entry in the user's medical records that is responsive to the medical question; sending the at least one identified scripted message to the second user from the first user by the first user device, wherein the at least one identified scripted message comprises a reply to the information in the received message; and
in response to the received message, sending the reply message and a plurality of scripted replies to the reply message, wherein the plurality of scripted replies include recommended responses to the reply message.

2. The method according to claim 1, further comprising:
searching a user's calendar when the at least one keyword indicates a scheduling question;
identifying at least one available time slot in the user's calendar; and
one of automatically sending a message identifying the at least one available time slot to the second user and displaying the at least one available time slot to the first user.

3. The method according to claim 1, further comprising:
automatically sending a message including the at least one entry in the user's medical records to the second user.

4. The method according to claim 1, further comprising determining an optimum time to send a message to a recipient based on a response history of the recipient.

5. The method according to claim 1, wherein said sending of the at least one identified scripted message to the second user includes:
displaying the at least one identified scripted message to the first user;
receiving at least one selected scripted message from the first user; and
sending the at least one selected scripted message to the second user.

6. The method according to claim 1, wherein the sending is performed in response to receiving the message from the second user.

7. The method according to claim 1, wherein receiving by the first user at the interface of the first user device the message sent from the second user to the first user further comprises:
receiving the message from the second user in response to a monitoring device identifying a change to a profile of a user based on user medical data, and triggering a chat with the first user and identifying in the electronic database the at least one scripted message that includes a response which corresponds to the change in the profile.

8. A system for sending a message from a first user to a second user, said system comprising:
an interface of a first user device configured to receive a message sent from the second user to the first user;
a processor connected to said interface, said processor being configured to identify at least one keyword in the message and search an electronic database for the at least one keyword to identify a reply message to the received message, wherein the reply message comprises at least one scripted message having contents corresponding to a response to information contained in the received message, said electronic database being connected to said processor, said electronic database including scripted messages for each keyword in said electronic database, wherein the scripted messages comprises replies to the information in the received message, and wherein identifying the reply message comprises identifying at least one entry in the user's medical records that is responsive to the medical question;
a communications device of the first user device connected to said processor, said communications device configured to, in response to the received message, sending the reply message and a plurality of scripted replies to the reply message, wherein the plurality of scripted replies include recommended responses to the reply message.

9. A system for sending a message from a first user to a second user, said system comprising:
an interface of a first user device configured to receive a message sent from the second user to the first user;
a processor connected to said interface, said processor being configured to identify at least one keyword in the message and search an electronic database for the at least one keyword to identify at least one scripted message having contents corresponding to a response to information contained in the received message, said electronic database being connected to said processor, said electronic database including scripted messages for each keyword in said electronic database; and
a communications device of the first user device connected to said processor, said communications device configured to send the at least one identified scripted message to the second user,
wherein the electronic database includes scripted replies to the scripted messages, wherein said sending of the at least one scripted message to the second user includes sending a plurality of scripted replies to the scripted message to the second user.

10. The system according to claim 8, wherein said communications device automatically sends a message including the at least one entry in the user's medical records to the second user.

11. The system according to claim 8, wherein said processor determines an optimum time to send a message to a recipient based on a response history of the recipient.

12. The system according to claim 8, wherein the scripted replies to the scripted messages are presented to the second user on a user interface for selection to be transmitted in response to the scripted messages.

13. The system according to claim 12, wherein the user interface is dynamically adjusted based on the type of the scripted replies.

14. The system according to claim 8, wherein receiving the message sent from the second user to the first user further comprises:

receiving the message from the second user in response to a monitoring device identifying a change to a profile of a user based on user medical data, and triggering a chat with the first user and identifying in the electronic database the at least one scripted message that includes a response which corresponds to the change in the profile.

15. A non-transitory computer-readable medium having computer-readable instructions stored thereon which when executed by a computer cause a computer to perform a method for sending a message from a first user to a second user, said method comprising: receiving by a first user at an interface of a first user device a message sent from the second user to the first user;
   identifying at least one keyword in the message by a processor;
   searching an electronic database for the at least one keyword to identify a reply message to the received message, wherein searching the electronic database comprises searching a user's medical records when the at least one keyword indicates a medical question, wherein the reply message comprises at least one scripted message having contents corresponding to a response to information contained in the received message, the electronic database including scripted messages for each keyword in the electronic database, and wherein identifying the reply message comprises identifying at least one entry in the user's medical records that is responsive to the medical question;
   in response to the received message, sending the reply message and a plurality of scripted replies to the reply message, wherein the plurality of scripted replies include recommended responses to the reply message.

16. The non-transitory computer-readable medium according to claim 13, further comprising:
   searching a user's calendar when the at least one keyword indicates a scheduling question;
   identifying at least one available time slot in the user's calendar; and
   automatically sending a message identifying the at least one available time slot to the second user and display the at least one available time slot to the first user.

17. The non-transitory computer-readable medium according to claim 16, further comprising:
   searching a user's medical records when the at least one keyword indicates a medical question;
   identifying at least one entry in the user's medical records that is responsive to the medical question; and
   automatically sending a message including the at least one entry in the user's medical records to the second user.

18. The non-transitory computer-readable medium according to claim 15, further comprising:
   searching a user's calendar when the at least one keyword indicates a scheduling question;
   identifying at least one available time slot in the user's calendar; and
   automatically sending a message identifying the at least one available time slot to the second user and display the at least one available time slot to the first user.

19. The non-transitory computer-readable medium according to claim 18, further comprising:
   automatically sending a message including the at least one entry in the user's medical records to the second user.

20. The non-transitory computer-readable medium according to claim 15, wherein receiving by the first user at the interface of the first user device the message sent from the second user to the first user further comprises:
   receiving the message from the second user in response to a monitoring device identifying a change to a profile of a user based on user medical data, and triggering a chat with the first user and identifying in the electronic database the at least one scripted message that includes a response which corresponds to the change in the profile.

* * * * *